United States Patent

Nicolas et al.

[11] Patent Number: 5,820,901
[45] Date of Patent: Oct. 13, 1998

[54] TEA EXTRACT PREPARATION

[75] Inventors: Pierre Nicolas, Saint-Legier; Eric Raetz, Lausanne; Sylviane Reymond, Epalinges; Jean-Luc Sauvageat, Morges, all of Switzerland

[73] Assignee: Nestec S.A., Vevey, Switzerland

[21] Appl. No.: 760,620

[22] Filed: Dec. 4, 1996

[30] Foreign Application Priority Data

Dec. 7, 1995 [EP] European Pat. Off. .............. 95203391

[51] Int. Cl.$^6$ ...................................... A23F 3/00
[52] U.S. Cl. ................ 426/49; 426/52; 426/597
[58] Field of Search ............................... 426/49, 52, 597, 426/590

[56] References Cited

U.S. PATENT DOCUMENTS

| | | | |
|---|---|---|---|
| 3,812,266 | 5/1974 | Sanderson et al. | 426/52 |
| 3,959,497 | 5/1976 | Takino | 426/52 |
| 4,051,264 | 9/1977 | Sanderson et al. | 426/52 |
| 4,217,338 | 8/1980 | Quash | 424/1 |
| 5,258,188 | 11/1993 | Barmentlo et al. | 426/52 |
| 5,445,836 | 8/1995 | Agbo et al. | 426/52 |

FOREIGN PATENT DOCUMENTS

| | | |
|---|---|---|
| 0 391 468 | 3/1990 | European Pat. Off. . |
| 1 249 932 | 10/1971 | United Kingdom . |
| 1 380 135 | 1/1975 | United Kingdom . |

OTHER PUBLICATIONS

Biotechnology and Bioengineering, vol. 16, No. 8, 1974, pp. 1095–1102, "Immobilized Tannase" by H. Weetall et al.

Biotechnology and Bioengineering, vol. 26, 1984, pp. 1223–1226, "Invertase Immobilisation" by M. Marek et al.

Primary Examiner—Leslie Wong
Attorney, Agent, or Firm—Pennie & Edmonds LLP

[57] ABSTRACT

Tannase covalently immobilized by its glycoside part on an insoluble support. Process for the preparation of a tea extract, in which an aqueous extract of tea leaves is prepared, and the extract is treated at a temperature of 20–65° C. with tannases whose glycoside part is covalently immobilized on an insoluble support, in particular in a tank which contains immobilized tannases in suspension, or in a reactor which includes a fixed bed or a fluidized bed of immobilized tannases.

11 Claims, 2 Drawing Sheets

TEA EXTRACT PREPARATION

The present invention relates to an immobilized tannase comprising any tannase covalently immobilized, via its glycoside part, on an insoluble support, as well as to a new process for the preparation of a tea extract which makes it possible to solubilize tea cream.

STATE OF THE ART

Black tea, which is used for the preparation of hot and cold drinks, is traditionally prepared by subjecting fresh green tea leaves to various treatments, including a step of fermentation of the leaves by oxidative enzymes. This fermentation step is essential for obtaining the compounds which confer the characteristic organoleptic and color qualities on black tea. When black tea is extracted with hot water, a precipitate appears upon cooling to temperatures of less than 55° C., or even 60° C., due to the formation of partially insoluble complexes of esters of polyphenols and of caffeine. The insoluble components are commonly designated by the expression "tea cream" or "cream".

The preparation of a cold drink based on black tea thus requires the removal of the tea cream. EP198209 (Société des produits Nestlé S.A.) thus proposes subjecting black tea leaves to extraction with water at 60–130° C., which gives a first extract which is separated from the tea leaves, concentrated to a solids content of 5–12.5% and then cooled to 5–15° C. in order to form an insoluble cream which is separated from the first concentrated extract, and which is then subjected to extraction with water at 40–70° C., giving a second extract which is separated from the remaining insoluble cream, the first and second extracts then being mixed. The disadvantage of this process is that solids are removed. Furthermore, the removal of the cream causes a significant loss of aroma.

To overcome these problems, it has been envisaged using a tannin acyl hydrolase, commonly called tannase, to hydrolyse the polyphenol esters, especially the polyphenol gallates, which form a complex with caffeine and form tea cream. Although tannases indeed make it possible to substantially reduce the formation of tea cream, their use is hampered by the high cost of the enzymes as well as by their instability at temperatures greater than 40° C. (Thomas R. L. et al., Journal of Food Science, 50, 1126–1129, 1985).

In order to get around the cost and the instability of the enzyme, GB 1,380,135 (Unilever N.V.) proposes treating at high temperature an aqueous tea extract with tannases covalently immobilized, via their peptide part, on an insoluble support. The temperatures used are generally of the order of 50° C., so as to be able to treat the cream before precipitation. Unfortunately, the immobilized enzyme substantially loses its activity after few passes of its substrate, which is economically and industrially scarcely profitable. Other advantages are mentioned in EP 0,391,468 (Unilever N.V.), such as an insufficient solubilization of the cream. A substantial release of the enzymes from the support is also frequently observed.

Likewise, U.S. Pat. No. 4,051,264 (Lipton Inc.) proposes directly treating thinly sliced green tea leaves with free tannases or tannases covalently immobilized via their peptide part, under anaerobic conditions, at a temperature and for a time sufficient to enhance the extractability of the leaves at cold temperature, fermenting the leaves in order to obtain black tea leaves, and heating them until their moisture content is less than 5%. It may also be noted that the reaction temperature for the immobilized enzymes cannot be greater than 40° C. without causing a substantial loss of enzymatic activity (see Table 4 of the abovementioned patent).

SUMMARY OF THE INVENTION

The aim of the present invention is to overcome the disadvantages of the prior art. To this end, the invention relates to an immobilized tannase comprising any tannase covalently immobilized, via its glycoside part, on an insoluble support.

The invention also relates to a process for the preparation of a tea extract, in which an aqueous extract of tea leaves is prepared, and the extract is treated at a temperature of 20–65° C. with an immobilized tannases whose glycoside part is covalently immobilized on an insoluble support.

The immobilized tannases according to the invention have the advantage of being particularly stable over time at temperatures greater than 50° C. or 55° C., or even 60° C. It can thus be shown that the tannase according to the invention has a critical temperature above which it becomes unstable, which is 15° C. to 25° C. greater than that of the free enzyme. This is particularly exceptional in the field of immobilized enzymes.

Another advantage consists in the fact that no release of the tannase from the support is observed and that the enzyme is still active after at least 400 passes of its substrate. This stability over time is very surprising and is not at all predictable, in particular when it is compared with that of the immobilized tannase of GB 1,380,135 or U.S. Pat. No. 4,051,264.

Another advantage of the present process is that it is possible to work at a temperature which is unfavorable to bacterial development, thus improving the biological hygiene conditions of the process.

Another advantage of the present process is that at temperatures of 55° C. to 70° C. the tea cream is particularly soluble, which allows the immobilized tannases to hydrolyse the polyphenolic complexes better. The difficult, if not impossible, transfer of solid material is thus avoided, thereby greatly enhancing the speed and the final yield of solubilization of the cream.

Finally, the present invention also has the advantage that a tea extract can be hydrolysed in a stirred tank type reactor and in a reactor comprising a fixed bed or a fluidized bed of immobilized supported tannases.

In the description which follows, "stirred tank type reactor" is understood to mean a mechanically stirred system comprising immobilized tannases in suspension. "A fixed bed of immobilized tannases" is also understood to mean tannases immobilized on or in a support which is compacted in a reactor intended for the continuous treatment of a liquid tea extract. Likewise, "a fluidized bed of immobilized tannases" is understood to mean tannases immobilized on a support, which is placed but not compacted in a reactor intended for the continuous treatment of a liquid tea extract. The stream of tea extract, circulating from the bottom to the top, then brings about the suspension of the support particles.

Black tea and Oolong tea are understood to mean, respectively, the product of the complete and partial enzymatic oxidation of green tea leaves obtained from the tea tree *Camellia*, especially *C. sinesis* and *C. assaimica*. Members of the genus *Phyllanthus, Catechu, Gambir* or *Uncaria* can also be used.

Finally, the unit of tannase is defined as the quantity of tannase which hydrolyses 1 µmol of methyl gallate in 1 min at pH 5 and at 30° C.

DETAILED DESCRIPTION OF THE INVENTION

To carry out the present process, tea leaves obtained from any species of the tea tree, and more particularly black or Oolong tea leaves, are extracted with water. The aqueous tea extract may thus be prepared by any method known to persons skilled in the art for extracting tea leaves. For example, 2 to 25 parts by weight of water, preferably 4 to 15 parts by weight, and in particular 5 to 12 parts by weight per part by dry weight of tea leaves may be used. The duration of the extraction may be conventionally, for example, up to 30 min, preferably from 2 to 15 min and particularly from 5 to 12.5 min. The temperature of the water may be conventional, for example up to 130° C., preferably from 60° C. to 125° C., and in particular from 75° C. to 120° C., or even from 85° C. to 110° C.

The extraction of the leaves may be carried out in a stirred tank comprising water and the leaves. The extraction may also be carried out continuously, by percolation or in a countercurrent system in which the water passes in the opposite direction to gravity in cells comprising the tea leaves. The teachings relating to the preparation of a tea extract described in EP198209, EP481262, EP654221 and EP95202228.3 is incorporated by reference into the description of the present invention.

The tea leaves may then be separated and the aqueous extract comprising 1% to 11% by weight of solids treated by any processes known to persons skilled in the art, such as for example concentrating until 5 to 15% by weight of tea extracts are obtained. The cream part of the extract can also be concentrated by cooling the extract to 4° C.–20° C. so as to cause the cream to appear, and then by separating the cream by filtration or centrifugation for example. It is also possible to carry out a resolubilization of the separated cream with hot water, preferably at 60° C.–80° C.

It is also possible to carry out an extraction of the flavors which will be reincorporated into the extract at the end of the process for example.

Finally, the aqueous extract comprising the cream which it is desired to solubilize by the tannases may have a dry matter content of 1% to 30%, preferably 1 to 20%.

The extract is then treated with tannases whose glycoside part is covalently immobilized on an insoluble support. The tannase used is a glycoprotein known to hydrolyse the gallic acid esters of the polyphenolic compounds of tea. The tannase may be obtained from certain fungi of the genus *Aspergillus* such as for example *Aspergillus niger*, *Aspergillus flavus* or *Aspergillus oryzae*, or of the genus *Penicillium* such as, for example, *Penicillium chrysogenum*, or alternatively yeasts of the genus *Candida*. Two strains of microorganisms are known to produce substantial quantities of tannase, such as *Aspergillus oryzae* ATCC No. 9362 and *Aspergillus niger* ATCC No. 16888. Tannases may also be commercially obtained in purified powdered form, for example from the company Enzyme Development Corporation (Tannase S®, N.Y., USA), or Kikkoman (Tannase Kikkomann 50000U/g®, Japan).

Preferably, the support chosen has pores having a mean diameter of the order of 20–2000 nm, especially 50–1000 nm. It may be an inorganic support which may be chosen from the group consisting of particles of silica, glass, metallic oxides such as alumina, or natural minerals such as bentonite for example. It may also be an organic support which may be chosen from the group consisting of polysaccharides such as cellulose, dextran or chitin, proteins such as silk, or synthetic polymers of the type comprising polystyrene, polyacrylate, polymethacrylate such as Eupergit® (Röhm, Germany), polyvinyl and polyamide such as nylon for example.

The support may be activated by introducing therein groups capable of binding to the oxidized glycoside part of the tannase, for example free amine groups or hydrazide groups. Numerous methods of activating supports are known to persons skilled in the art who will thus be able to choose, according to the supports, the active groups which are suitable for binding with the glycoside part of the tannase. By way of example, the immobilization method described by Marek et al. will be followed (Biotechnology and Bioengineering, 26, 1223–1226, 1984).

The tannase can also be modified beforehand, for example by oxidizing it in a conventional manner. It can thus be oxidized with a 0.01–1M solution of periodate at pH 4–6 for 1 to 120 min at a temperature of 0° C. to 25° C. The oxidation reaction may be stopped by adding a reducing solution, such as for example a solution at 1–3M ethylene glycol. Preferably, the oxidized tannase is then cleaned from the oxidizing or stopping solutions, for example by dialysis in a suitable buffer, especially a 0.01–1M sodium phosphate buffer pH 5–7.

The oxidized tannase may be immobilized on a support capable of reacting with the aldehyde groups thus created. To do this, Eupergit-C® may be modified by a 0.1–1M solution of adipic dihydrazide at pH 4–9, by a 0.1–1M solution of ethylenediamine pH 4–9, or by a 0.1–1M solution of hexamethylenediamine pH 4–9 for example. For that, 1 g equivalent dry weight of modified support can be mixed with at least 10 mg of oxidized tannase, preferably 20–300 mg, for 1 to 30 h, at 4–30° C., for example.

In the case of coupling by diamines, the imine bond can also be consolidated by reducing with sodium borohydride or cyanoborohydride.

In the final analysis, it is preferable to inactivate the remaining functional groups by techniques known to persons skilled in the art. However, this inactivation step is not essential for obtaining an active immobilized tannase.

The tannase may be immobilized on the support in an amount of at least 10 mg of tannase per g of support, preferably 20–100 mg. The activity of the immobilized tannase may be at least 40 tannase units per g of support, for example 40–200 units.

When a tea extract is hydrolysed with the immobilized tannase according to the invention, an adsorption of components of the tea on the support may be observed at the start of the use of the enzyme. These components may unfortunately be involved in the color and taste of the tea. It may therefore be preferable to use an immobilized tannase according to the invention which has been preincubated at least once in a tea extract.

In a first preferred embodiment of the present invention, the tea extract is hydrolysed in a stirred tank type reactor, with an immobilized tannase according to the invention. The system may be automated and may operate in a semicontinuous mode with the following three phases. First, the tank is filled with the tea extract to be treated, then hydrolysis is carried out with mechanical stirring, and finally the tank is emptied after a defined period. The retention of the enzyme in the reactor may be achieved by means of a filter placed in the lower part of the tank. This filter can retain any particle with a diameter greater than 40 μm for example. To treat the tea extract, 1 part by weight of extract may be mixed in the tank with less than 1 part by weight of support, for example 0.0001–0.1 part of support, and then the mixture incubated with stirring at 20–65° C. for 10–200 min, preferably 50–65° C., or even 55–65° C., for 10–100 min, for example.

According to this method of hydrolysis, it may be observed that the immobilized tannases according to the invention have a remarkable stability, because they conserve 100% of their enzymatic activity after numerous reuses up to 60° C., especially for 5–420 cycles of 30 min at a temperature of 30° C. to 60° C., the large numbers of cycles corresponding to the low temperatures and conversely. Finally, at 65° C., the enzyme slowly loses its activity over time, which preferably marks its upper limit for use.

In a second preferred embodiment of the present invention, the liquid tea extract is continuously hydrolysed in a reactor comprising a fixed bed of immobilized tannases according to the invention. Preferably, at least 1 part by weight of extract is passed per part by weight of bed, for example 10–10,000 parts of extract, at a temperature of 20–65° C., preferably 50–65° C., or even 55–65° C.

In a third preferred embodiment of the present invention, the liquid tea extract is continuously hydrolysed in a reactor comprising a fluidized bed of immobilized tannases according to the invention. Preferably, at least 1 part by weight of extract is passed per part by weight of bed, for example 10–10,000 parts of extract, at a temperature of 20–65° C., preferably 50–65° C., or even 55–65° C.

The extract thus treated may still have insolubles which the tannases have not been able to solubilize even after total hydrolysis by the immobilized tannases according to the invention. It may therefore be necessary to separate them by filtration or centrifugation after having cooled the extract to 4–20° C. for example. This operation, conventionally called "polishing" has already been described in GB 1,380,135 and EP391468.

The treated extract may then be used traditionally in the preparation of an instant tea powder. If the extract is obtained directly from a crude extract of tea leaves, it can be concentrated and dried, for example by freeze-drying or by spray-drying for example. If the extract is obtained from tea cream previously separated from the crude extract of tea leaves, it can be mixed with the crude extract and then concentrated and dried.

The tea powder reconstituted with water preferably comprises 0.25–0.3% by weight of tea solids and has a pH of 4.5–5.5. It has a turbidity, measured at 10° C., in "Nephelometric Turbimetric Units" (NTU), for example with a Hatch Ratio Turbimeter® (Hatch Company, Colorado, USA), which is less than 50 NTU, preferably less than 35 NTU, for example 5 to 15 NTU. The tea powder obtained by the process according to the present invention is a product comprising only tea extracts, which is instantly soluble in cold water, giving a drink whose color and taste are particularly stable over time and appreciated by tasters.

EXAMPLES

The examples below are given by way of illustration of the process and of the immobilized tannase according to the present invention. In these examples, the tannase marketed under the trademark Kikkoman 50000U/g® is used, and in some of these examples, a solution of methyl gallate which makes it possible to evaluate conveniently and precisely the excellent stability of the immobilized tannase preparation according to the invention is used as model substrate. These examples are preceded by a method for determining the enzymatic activity of the tannase, a method for measuring gallic acid in tea and a presentation of the drawings.

Enzymatic Activity of the Tannase

The activity of the tannase is determined by measurement, using high-performance liquid chromatography (HPLC), of the gallic acid released by hydrolysis of methyl gallate. For that, 0.5 ml of enzyme solution is mixed with 1.5 ml of a 20 mM solution of methyl gallate in 50 mM of an acetate buffer pH5. In practice, the samples of enzymes- are diluted before incubation so that the gallic acid concentration does not exceed 1 mM at the end of the reaction.

The mixture is incubated at 30° C. for 15 min, the reaction is stopped with 0.2 ml of 2M HCl, 10 µl are injected into a reversed phase KS 250/6/4 Nucleosil® 100-5 C18 column (Macherey-Nagel GmbH, Düren DE) having as a mobile phase 2% acetic acid:acetonitrile (78:22 v/v), and elution is carried out under isocratic conditions, at a speed of 1 ml/min, with a spectophotometric detection at 278 nm.

Measurement of the Gallic Acid

The gallic acid produced in the tea by the tannase is determined by HPLC with the same column as that described above, using the following gradient, at a speed of 1 ml/min: 0–5 min: 88% A and 12% B; 5–16 min; 75A and 25% B; 16–25 min: 88% A and 12% B (A=acetic acid 2%; B=acetonitrile).

COMPARATIVE EXAMPLES

Figure 1:
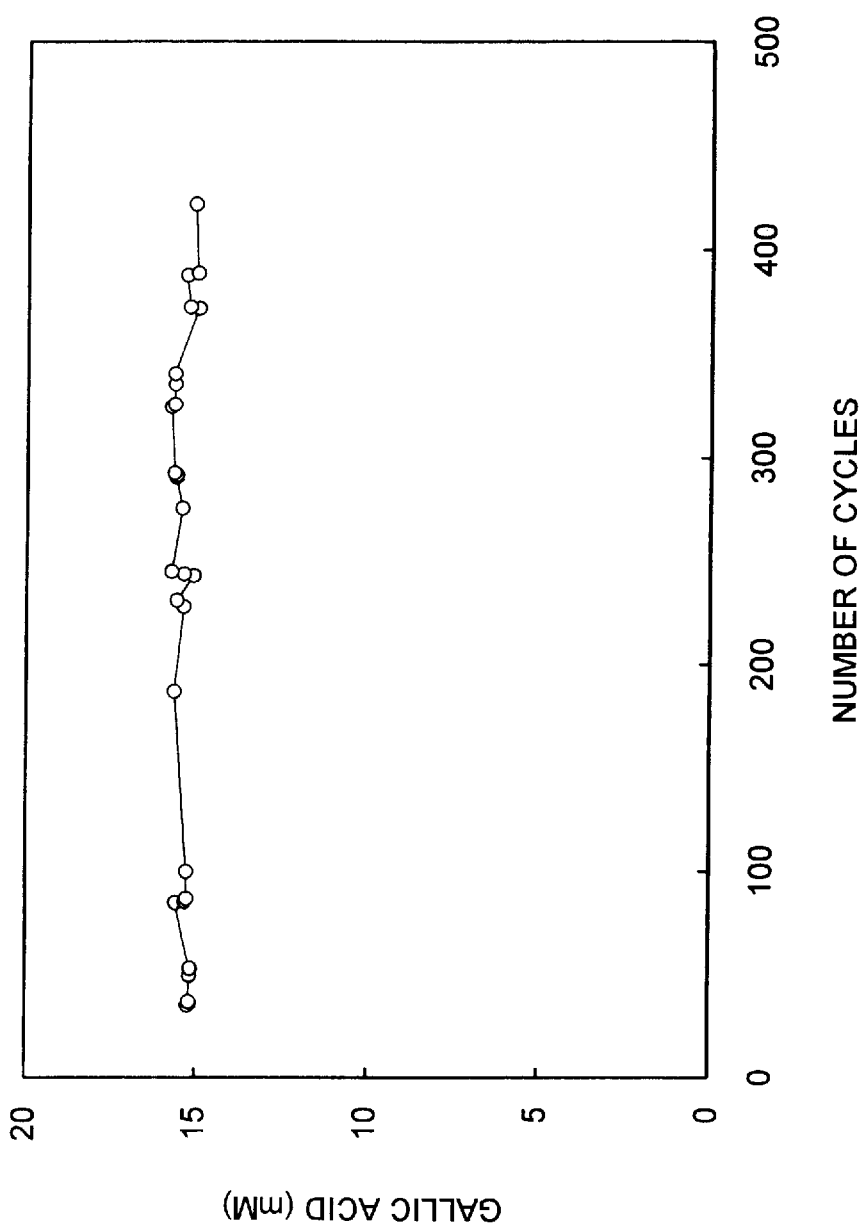
FIG. 1 graphically illustrates the release of gallic acid as a function of the number of hydrolysis cycles in a "stirred tank" type reactor at 30° C.

A conventional means of immobilizing the enzymes on Eupergit® is to react the amine residues of the protein part of the enzyme with the oxirane groups of the support. The reaction is initiated by phosphate concentrations of 1M under conditions similar to those presented in Example 3 of EP676145.

It was observed that it is not possible to immobilize the tannase Kikkoman 50000U/g® on various Eupergit® supports under the conditions presented in Table 1. This was found to occur even when the tannase is dialysed in order to purify it or when Eupergit-C® with larger pores or which is nonporous is used to allow easier access of the tannase to the oxirane groups of the support.

The tannase is not therefore an enzyme which can be easily covalently immobilized by its peptide part. This may explain in part the fact that the immobilized tannases described in the prior art have disadvantages which make them industrially and economically unattractive (see EP391468).

TABLE 1

|  | Test 1 | Test 2 | Test 3 | Test 4 |
|---|---|---|---|---|
| Support | Eupergit-C® | Eupergit-C® | Eupergit 250L® | Eupergit-C12® |
| Limit of exclusion | 200 kD | 200 kD | 1000 kD | non porous |
| Concentration of support (dry) | 133 g/l | 133 g/l | 133 g/l | 75-125-250 g/l (three tests) |
| Concentration of tannase (protein) | 10 g/l | 10 g/l | 10 g/l | 4 g/l |

TABLE 1-continued

|  | Test 1 | Test 2 | Test 3 | Test 4 |
|---|---|---|---|---|
| Medium | 1M potassium phosphate pH6 | 1M potassium phosphate pH 7.5 | 1M potassium phosphate pH6 | 1M potassium phosphate pH6 |
| Reaction time | 70 h | 48 h | 48 h | 48 h |
| Reaction temperature | 22° C. | 22° C. | 22° C. | 22° C. |
| Prior dialysis | NO | YES | NO | YES |
| Immobilization of the tannase | NO | NO | NO | NO |

Example 1

The tannase Kikkomann 50000U/g® is oxidized with periodate under controlled conditions. For that,. 4.5 ml of a 0.1M sodium acetate buffer pH 5.5 comprising 22.22 g/l of a tannase powder are mixed with 0.5 ml of a 0.1M sodium acetate buffer pH 5.5 comprising 0.1 mM sodium periodate. The mixture is allowed to oxidize at 0° C. for 60 min in the dark, the reaction is stopped by adding 0.5 ml of a 2M solution of ethyleneglycol, and then the mixture is dialysed in a 0.1M sodium phosphate buffer pH6 at 4° C.

On the other hand, 20 ml of a 0.2M sodium phosphate buffer comprising 0.2M adipic dihydrazide pH 8 are mixed with 1 g of dry Eupergit-C®. The mixture is incubated at room temperature with gentle stirring for 16 h, and then the support is thoroughly washed with distilled water and then with a 0.1M sodium phosphate buffer pH6.

1 g equivalent dry weight of wet modified Eupergit-C® is then mixed with 5.4 ml of oxidized tannase solution, the mixture is incubated at 4° C. with gentle stirring for 16 h, the support is washed in a 0.1M sodium phosphate buffer pH6. The support finally has 20 mg of tannase protein per g of dry support.

Example 2

40 ml of substrate, consisting of 20 mM methyl gallate in a 50 mM sodium acetate buffer pH 5, are treated with 150 mg equivalent dry weight of immobilized tannase of Example 1 in a traditional reactor of the stirred tank type. The quantity of tannase is then adjusted in order to obtain 75% hydrolysis of the substrate in 30 min.

This reactor comprises in particular a tubular glass body whose lower part comprises a filter with a porosity of about 40 $\mu$m, connected to a peristaltic pump intended to collect the hydrolysed product, and whose top part comprises the outlet of a peristaltic pump intended for the introduction of the substrate. The reactor is immersed in a water bath at 30° C.

In the first instance, the substrate is introduced into the reactor for about 110 s, and then it is mixed for 27 min and 20 s, and finally the reaction medium is collected for 50 s. 420 successive cycles of about 30 min are performed, and the quantity of gallic acid released in the reaction medium is measured for each cycle by the HPLC method described above. The results presented in FIG. 1 show that the immobilized tannase of Example 1 preserves 100% of its activity after 420 successive hydrolysis cycles at 30° C.

Example 3

1 g of dry Eupergit-C® is mixed with 20 ml of a 0.3M sodium phosphate buffer comprising 0.175M ethylene diamine pH8, the mixture is incubated at room temperature with gentle stirring for 16 h, it is thoroughly washed with distilled water and then with a 0.1M sodium phosphate buffer pH6. Eupergit-C® modified by ethylenediamine is obtained.

1 g equivalent dry weight of modified wet Eupergit-C® is mixed with 5.43 ml of the solution of oxidized tannase described in Example 1, the mixture is incubated at room temperature with gentle stirring and for 16 h, and then the support is washed in a 0.1M sodium phosphate buffer pH6. Eupergit-C® comprising 25 mg of tannase protein per g of dry support is obtained.

Example 4

40 ml of substrate of Example 2 are treated at 30° C. with 148 mg equivalent dry weight of immobilized tannase of Example 2 in the reactor described in Example 2. This quantity is reduced to 88 mg for the cycles from 25° to 65° C.

There are carried out successively 139 cycles at 30° C., 61 cycles at 35° C., 189 cycles at 40° C., 42 cycles at 45° C., 10 cycles at 50° C., 37 cycles at 55° C., 8 cycles at 60° C. and 8 cycles at 65° C.

Figure 2:
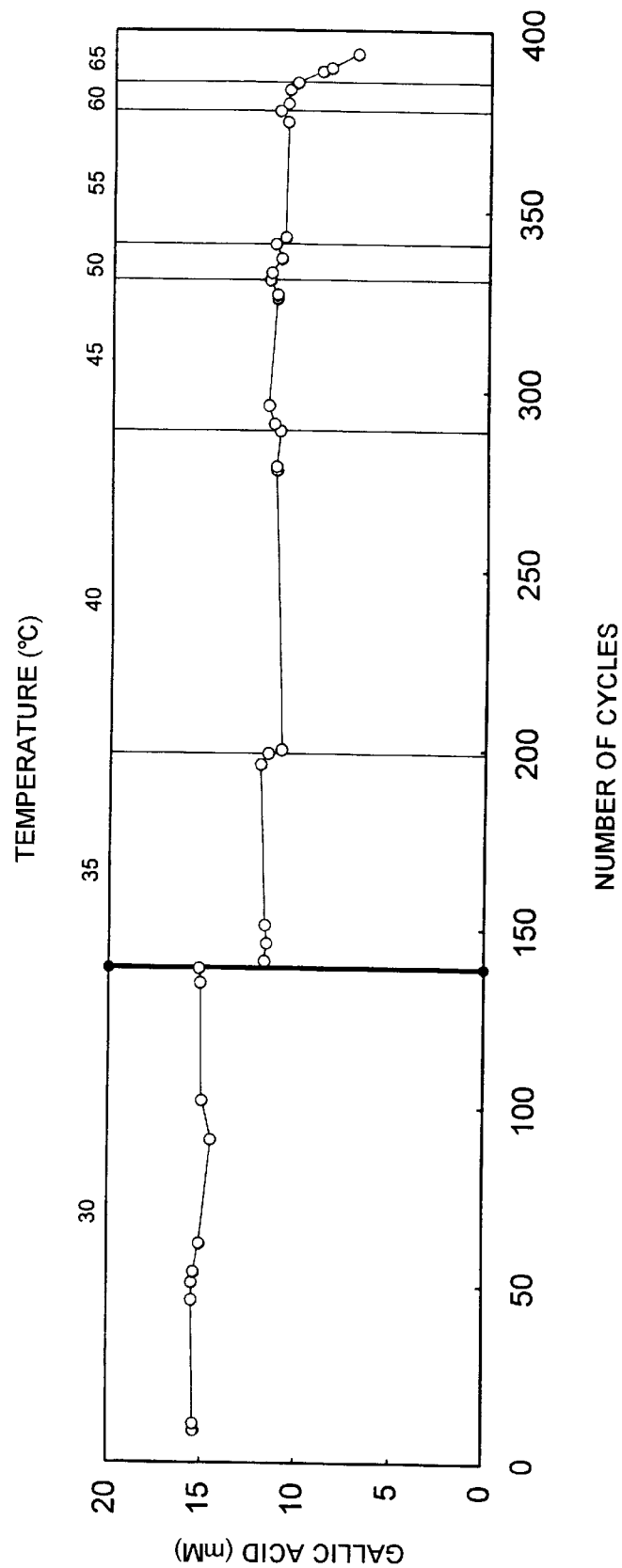
FIG. 2 graphically illustrates the release of gallic acid as a function of the number of hydrolysis cycles in a "stirred tank" type reactor at temperatures varying from 30° C. to 65° C.

The results presented in FIG. 2 are similar to those presented in FIG. 1, namely the immobilized tannase of Example 3 preserves 100% of its activity after 139 successive hydrolysis cycles at 30° C. The surprising stability of the immobilized tannase of Example 3 over time and at the temperature may however be noted. Indeed, the enzyme preserves practically 100% of its activity up to 60° C. under conditions of intensive use of the enzyme. Finally, at 65° C., the enzyme slowly loses its activity over time.

For comparison, the free tannase rapidly loses its activity at a temperature greater than 40° C. (Thomas et al).

Example 5

A tea extract is prepared by mixing 1 kg of black tea leaves of good quality (Darjeeling FOP) with 15 litres of deionized water at 95° C. for 10 min and by separating the tea leaves by hot filtration through a 40 $\mu$ filter. An extract containing 2.29% solids is thus obtained.

Immobilized tannase is prepared in larger quantities according to the procedure described in Example 3, and it is rinsed several times with the above tea extract in order to saturate and equilibrate the preparation.

15 g of this wet immobilized tannase are added to 1 litre of extract at 55° C. The mixture is stirred for 1 h at 55° C. and then the extract is separated by filtration through a 40 $\mu$ filter. The immobilized tannase is thus recovered so as to be reused 3 times consecutively with the same initial extract and under the same conditions. The extracts are adjusted to pH 5 with a solution of sodium hydroxide and then cooled to 4° C. and the quantity of insoluble matter formed is measured and compared with that produced in the untreated initial extract.

Table 2 below indicates the results obtained. It may be observed that the treatment allowed a substantial reduction in the quantity of tea cream and this even after reusing the immobilized tannase.

TABLE 2

|  | % total solids in the extract | % insolubles at 4° C. (based on the total solids) | % nonsolubilised solubles at 4° C. | Gallic acid released (g/l) |
|---|---|---|---|---|
| Untreated | 2.29 | 28.7 | 100 | — |
| 1st treatment | 2.29 | 4.24 | 14.8 | 2.19 |
| 2nd treatment | 2.29 | 4.20 | 14.6 | 2.17 |
| 3rd treatment | 2.29 | 4.30 | 15.0 | 2.19 |
| 4th treatment | 2.29 | 4.20 | 14.6 | 2.17 |

The four treated extracts are combined and centrifuged, when cold, at 10,000 revolutions/min for 15 min. The supernatant is evaporated and then freeze-dried. A tea powder is thus obtained which has, upon reconstitution, very good solubility in cold water, the red-brown colour typical of a tea extract and the taste characteristic of a black tea which has preserved its natural astringency. The turbidity of the drink is less than 30 NTU.

Example 6

The black tea leaf extract of Example 5 is used, this being passed through a column maintained at 55° C., and containing 25 g of wet immobilized tannase of Example 5. The extract is pumped at a speed of 1 l/h and, after equlibrium, is recovered at the outlet of the column. An aliquot of 1 l is adjusted to pH 5 with a solution of sodium hydroxide and then cooled to 4° C.

After cold centrifugation, the supernatant is separated, concentrated and freeze-dried. A powder is thus obtained which is completely soluble when cold and which has the taste and the colour desired by tasters. The turbidity of the drink is less than 30 NTU.

What is claimed is:

1. Process for the preparation of a tea extract, which comprises preparing an aqueous extract of tea leaves and treating the aqueous extract at a temperature of 20°–65° C. with an immobilized tannase whose glycoside part is covalently immobilized on an insoluble support.

2. Process according to claim 1, in which the tea extract is treated with an immobilized tannase having a support selected from the group consisting of organic, synthetic polymer or inorganic supports which have pores of 20–2000 nm.

3. Process according to claim 1, in which a tea leaf extract is prepared, the extract is cooled tea cream is separated, redissolved by heating, and then treated with the immobilized tannase.

4. Process according to claim 1, in which the tea extract treated with the immobilized tannases is dried.

5. Process according to claim 1, in which an aqueous extract of tea leaves is prepared, the extract is treated at a temperature of 50–65° C. in a tank comprising, in suspension, tannases whose glycoside part is covalently immobilized on an insoluble support.

6. Process according to claims 1, in which an aqueous extract of tea leaves is prepared, and the extract is continuously treated at a temperature of 50–65° C. in a reactor comprising a fixed bed of immobilized tannases.

7. Process according to claims 1, in which an aqueous extract of tea leaves is prepared, and the extract is continuously treated at a temperature of 50–65° C. in a reactor comprising a fluidized bed of immobilized tannases.

8. Process for the preparation of a tea extract, which comprises:

preparing an aqueous extract of tea leaves;

immobilizing a tannase on an insoluble support by covalently attaching the glycoside part of the tannase to the support to increase the number of cycles of use of the immobilized tannase; and treating the aqueous extract at a temperature of 20–65° C. with a sufficient amount of the immobilized tannase, wherein enzymatic activity of the immobilized tannase is retained over the increased number of cycles of treatment of such aqueous extracts at that temperature.

9. Process according to claim 8, wherein the immobilized tannase retains 100% of its enzymatic activity during 139 to 420 cycles of 30 minutes treatment at temperatures between 30 to 60° C.

10. Process for the preparation of a tea extract, which comprises:

preparing an aqueous extract of tea leaves;

immobilizing a tannase on an insoluble support by covalently attaching the glycoside part of the tannase to the support to increase the period of time in which the immobilized tannase has enzymatic activity;

preparing a fixed or fluidized bed of a sufficient amount of the immobilized tannase in a reactor; and continuously hydrolyzing the aqueous extract with the bed of immobilized tannase in the reactor at a temperature of 20–65° C., wherein enzymatic activity of the immobilized tannase is retained over the increased period of time of treatment at those temperatures compared to that of a tannase that is not immobilized.

11. Process according to claim 10, wherein at least 1 part by weight of extract is treated with 10–10,000 parts by weight of the immobilized tannase in the bed at a temperature of 50° to 65° C.

* * * * *